(12) United States Patent
Yao et al.

(10) Patent No.: US 6,673,975 B1
(45) Date of Patent: Jan. 6, 2004

(54) METHOD FOR PRODUCING 1,1-BIS-(4-HYDROXYPHENYL)-3,3,5-TRIMETHYLCYCLOHEXANE

(75) Inventors: Kazuhiko Yao, Wakayama (JP); Kenji Ekawa, Wakayama (JP); Yoichiro Isota, Wakayama (JP); Toru Nakaguchi, Wakayama (JP)

(73) Assignee: Honshu Chemical Industry Co., Ltd., Tokyo (JP)

( * ) Notice: Subject to any disclaimer, the term of this patent is extended or adjusted under 35 U.S.C. 154(b) by 0 days.

(21) Appl. No.: 10/380,099

(22) PCT Filed: Sep. 11, 2000

(86) PCT No.: PCT/JP00/06207

§ 371 (c)(1),
(2), (4) Date: Mar. 7, 2003

(87) PCT Pub. No.: WO02/22536

PCT Pub. Date: Mar. 21, 2002

(51) Int. Cl.⁷ .............................................. C07C 39/17
(52) U.S. Cl. ..................................................... 568/721
(58) Field of Search .......................................... 568/721

(56) References Cited

U.S. PATENT DOCUMENTS

| | | | |
|---|---|---|---|
| 5,227,458 A | * | 7/1993 | Freitag |
| 5,336,812 A | * | 8/1994 | Salek |
| 5,783,733 A | * | 7/1998 | Kissinger |
| 6,284,931 B1 | * | 9/2001 | Isota |

FOREIGN PATENT DOCUMENTS

| | | | |
|---|---|---|---|
| EP | 812815 | * | 12/1997 |
| EP | 995737 | * | 4/2000 |
| WO | WO-95-13259 | * | 5/1995 |

* cited by examiner

*Primary Examiner*—Michael L. Shippen
(74) *Attorney, Agent, or Firm*—Merchant & Gould P.C.

(57) ABSTRACT

The invention provides a process for production of high purity 1,1-bis(4-hydroxyphenyl)-3,3,5-trimethylcyclohexane (BPTMC) which comprises: (a) a reaction step wherein phenol is reacted with 3,3,5-trimethylcyclohexanone (TMC) in a slurry containing phenol adduct crystals of BPTMC in the presence of an acid catalyst; (b) a neutralization step wherein after the reaction, the resulting reaction mixture in the form of slurry is neutralized with an alkali while heating to convert the slurry to a solution; (c) a primary crystallization and filtration step wherein the resulting solution is cooled and the resulting phenol adduct crystals of BPTMC are collected by filtration; (d) a secondary crystallization and filtration step wherein the adduct crystals obtained in the primary crystallization and filtration step are heated in a crystallization solvent to dissolve the crystals therein to prepare a solution and then the solution is cooled to crystallize BPTMC out of the solution, followed by collecting the crystals of BPTMC by filtration; (e) a filtrate recycling step wherein at least a part of the secondary crystallization filtrate obtained in the secondary crystallization and filtration step is returned to the reaction step.

The process provides uncolored high purity BPTMC in high selectivity and in high yield in an industrially stable manner which is substantially free from residual phenol and trace impurities such as sodium, chlorine and sulfur and hence which is suitable for use as raw materials for the production of resins for optical use.

4 Claims, No Drawings

METHOD FOR PRODUCING 1,1-BIS-(4-HYDROXYPHENYL)-3,3,5-TRIMETHYLCYCLOHEXANE

TECHNICAL FIELD

The invention relates to a process for production of high purity 1,1-bis(4-hydroxyphenyl)-3,3,5-trimethylcyclohexane (referred to as "BPTMC" hereinafter) having stable quality in high yield and in high selectivity by an acid condensation reaction of phenol with 3,3,5-trimethylcyclohexanone (referred to as "TMC" hereinafter).

BACKGROUND ART

In recent years, BPTMC is used as raw materials for the production of optical products such as optical disks, as well as synthetic resins for optical use such as polycarbonate resins for optical use. A variety of processes for the production of BPTMC are already known. According to one of such processes, phenol is reacted with TMC using hydrogen chloride gas as a catalyst and an alkyl mercaptan as a promoter in the presence of an inactive organic solvent or in the absence of a solvent, and then phenol remained unreacted is removed from the reaction mixture by steam distillation, as described in Japanese Patent Application Laid-open No. 2-88634. It is also described therein that, after the reaction, water is added to the reaction mixture, and then an alkali to neutralize the reaction mixture, followed by heating, cooling and removing an aqueous phase, thereby obtaining the desired BPTMC as residue.

A further process is known, as is described in Japanese Patent Application Laid-open No. 8-505644. According to the process, phenol is reacted with TMC using hydrogen chloride gas as a catalyst and an alkyl mercaptan such as octanethiol as a promoter. After the reaction, water is added to the reaction mixture to form a slurry, and the slurry is filtered to provide 1:1 adduct crystals of BPTMC and phenol, and then the phenol is removed from the adduct crystals, thereby providing the desired BPTMC.

There is also known a process, as described in Japanese Patent Application Laid-open No. 4-282334, which provides the desired BPTMC by the reaction of phenol with TMC using water-insoluble cation exchange resins having sulfonic acid groups therein as a catalyst and a mercaptan compound as a promoter. In Japanese Patent Application Laid-open No. 5-213803, there is described a process in which an acid catalyst such as benzenesulfonic acid is added to a mixture of phenol, TMC, a mercaptan compound as a promoter and water, whereupon the reaction is started with stirring, and the desired BPTMC is obtained in high selectivity.

As mentioned hereinbefore, BPTMC is used as raw materials for polycarbonate resins for optical use. In order to supply BPTMC to this use, it is more and more strongly demanded to produce high purity BPTMC stably which is free of by-products derived from the reaction, and besides free of high boiling point by-products or colored by-products derived from purification processes for the obtained reaction product and residual phenol or trace impurities such as sodium.

In particular, it is most strongly demanded not only to suppress the generation of by-products such as isomers to improve the purity of the resultant BPTMC but also to reduce the amount of the residual phenol and trace impurities such as sodium, chlorine and sulfur derived from a catalyst or a promoter used in the reaction or an alkali used to neutralize the resultant reaction mixture as much as possible since such impurities give harmful influences on the resultant BPTMC when it is used as raw materials for polymers or when it is used for the production of electronic elements.

In general, in the production of BPTMC by an acid condensation reaction of phenol with TMC, the reduction of by-produced impurities such as isomers should be primarily achieved by improving the selectivity of the production of the desired product in the reaction. However, the impurities can be also reduced to a certain extent in a stage wherein the resultant reaction mixture is neutralized or in a stage wherein the resultant reaction product is purified. In fact, a variety of conditions under which the reaction mixture is neutralized or the reaction product is purified after the completion of the reaction have important significance in order to reduce the amount of trace impurities included in the resultant BPTMC.

Usually, in the reaction of phenol and TMC, the less the reaction temperature and the less the amount of reaction solvent used, the higher the selectivity of the reaction. But on the other hand, when the reaction temperature is low or the reaction solvent is used in a large amount, the reaction velocity is reduced inevitably, and besides, the reaction mixture increases in the viscosity as the reaction proceeds, resulting in difficult stirring. In addition, in the stage of neutralizing the resultant reaction mixture and of purifying the resultant reaction product, the improvement of purity of the reaction product and the reduction of impurities of the reaction product are contrary to each other in nature. Accordingly, it is very important to establish optimum combination of all the stages involved each having optimum operation conditions throughout the production stages in order to produce uncolored high purity BPTMC that is accompanied by impurities in a reduced amount as much as possible in a stable manner in high yields.

However, according to the known processes for production of BPTMC by the reaction of phenol with TMC, the selectivity of reaction is so small as about 70%, and besides no consideration has been heretofore paid to reduce the amount of trace impurities such as sodium included in the obtained product so long as the present inventors know.

Furthermore, according to the known processes, phenol is used usually in a large excess relative to TMC so that the filtrate obtained by filtering the reaction mixture after the reaction contains a large amount of phenol as well as BPTMC dissolved in the phenol and impurities such as isomers. Accordingly, it is also important to recover and reuse phenol or recover BPTMC from the resulting filtrate in order to produce advantageously BPTMC in an industrial scale.

On the other hand, a process for production of high purity 2,2-bis(4-hydroxyphenyl)propane (referred to as "bisphenol A" hereunder) is already described in, for example, Japanese Patent Application Laid-open No.5-392388, No.6-25048 or No. 6-25043.

In addition, with regard to bisphenol A, a process for production thereof including reuse of filtrate from a crystallization stage after the reaction is also proposed, for example, in Japanese Patent Application Laid-open No. 5-345737. According to the process, crystals of phenol adduct of bisphenol A are crystallized out of a phenol solution containing bisphenol A after the completion of the reaction, the crystals are collected by filtration, the resulting mother liquor is subjected to distillation to recover the phenol and the thus recovered phenol is recycled to the reaction stage. The bottom liquid in the distilling tower is heated and decomposed in the presence of an alkali catalyst. The resulting substance is recovered under a reduced pressure and purified by using an ion exchange resin, followed by recycle to the reaction stage.

In Japanese Patent Application Laid-open No. 6-321834, it is described that after phenol adduct crystals of bisphenol are crystallized and separated out of the reaction mixture, the resulting mother liquor is made contact with an acid catalyst to isomerize o- and p-isomers to p- and p'-isomers, and then the resulting isomers are returned to the crystallization stage for reuse.

Further in Japanese Patent Application Laid-open No. 10-59888, the following is described. Phenol is reacted with acetone in the presence of an ion exchange resin catalyst to produce bisphenol A, and the bisphenol A produced is led to a phenol removal unit to separate unreacted phenol therefrom. The obtained bisphenol A is led to a melt crystallizer to separate residual phenol and isomers therefrom. The separated phenol and isomers are cracked, and the thus recovered phenol is recycled to the reaction stage.

This process was proposed in consideration of the fact that in the production of bisphenol A, the filtrate from the crystallization stage contains by-products such as isomers or high molecular weight substances produced in the reaction stage so that when the filtrate is reused repeatedly, the by-products are concentrated and accumulated in the filtrate to contaminate the product, resulting in undesired coloration or deterioration in the quality of the product. According to this known process, therefore, the filtrate is first purified and is then recycled to the reaction stage.

However, it is difficult to predict the behavior of formation of BPTMC by a condensation reaction of TMC which is an alicyclic ketone having three methyl groups in the molecule with phenol based on the behavior of formation of bisphenol A by a condensation reaction of acetone and phenol. It is much more difficult to predict what each of the steps should be like and what the combination of the steps should be like in order to produce BPTMC which is not colored and substantially free from residual phenol or trace impurities such as sodium, chlorine and sulfur since there are remarkable differences not only in the reactivity of the ketones used but also in the production ratio of the desired products to by-products, solubility or melting points of the desired products, compositions of impurities contained in the desired products, among others.

Nothing is also known how to reuse effectively the filtrate that contains phenol and BPTMC dissolved therein obtained from the crystallization step of the reaction product formed.

Under these circumstances, there has been known no such process for the industrial production of uncolored high purity BPTMC that is substantially free from residual phenol or trace impurities such as sodium, chlorine and sulfur in high selectivity and in high yield in a stable manner.

The invention has been accomplished to solve such problems as involved in the known processes for the production of BPTMC by an acid condensation reaction of phenol and TMC.

Therefore, it is an object of the invention to provide a process suitable for industrial production of uncolored high purity BPTMC in high selectivity and high yield in a stable manner that is substantially free from residual phenol as well as trace impurities of sodium, chlorine and sulfur and hence is suitable for use as raw materials for the production of resins for optical use by making each of the steps of reaction, neutralization, primary crystallization and filtration, secondary crystallization filtration and filtrate recycling optimum and, in addition, establishing the optimum combination of these steps.

SUMMARY OF THE INVENTION

The invention provides a process for production of high purity 1,1-bis(4-hydroxyphenyl)-3,3,5-trimethylcyclohexane which comprises:

(a) a reaction step wherein phenol is reacted with 3,3,5-trimethylcyclohexanone in a slurry containing phenol adduct crystals of 1,1-bis(4-hydroxyphenyl)-3,3,5-trimethylcyclohexane in the presence of an acid catalyst;

(b) a neutralization step wherein after the reaction, the resulting reaction mixture in the form of slurry is neutralized with an alkali to a pH of 5 to 8 while it is heated so that it is converted to a solution;

(c) a primary crystallization and filtration step wherein the resulting solution is cooled and the resulting phenol adduct crystals of 1,1-bis(4-hydroxyphenyl)-3,3,5-trimethylcyclohexane are collected by filtration;

(d) a secondary crystallization and filtration step wherein the adduct crystals obtained in the primary crystallization and filtration step are heated in a crystallization solvent to dissolve the adduct crystals therein to prepare a solution and then the solution is cooled to crystallize the 1,1-bis(4-hydroxyphenyl)-3,3,5-trimethylcyclohexane out of the solution, followed by collecting the crystals by filtration;

(e) a filtrate recycling step wherein at least a part of the secondary crystallization filtrate obtained in the secondary crystallization and filtration step is recycled to the reaction step.

BEST MODE FOR CARRYING OUT THE INVENTION

The process for production of high purity BPTMC according to the invention will be now described in detail hereunder.

(Reaction Step)

In the reaction step of the process of the invention, phenol is reacted with TMC in the presence of an acid catalyst in a slurry comprised of phenol adduct crystals of BPTMC and hydrated phenol thereby to form phenol adduct crystals of BPTMC.

In order to carry out the reaction in the slurry in this manner, it is preferred that, for example, a mixture of phenol and water are placed in a reaction vessel before the reaction is started and, while the mixture of phenol and water (i.e., hydrated phenol), which is herein often referred to as the starting liquid mixture, is maintained at a temperature in the range of 15° C. to 40° C. at which phenol adduct crystals of BPTMC do not decompose nor are soluble in the starting liquid mixture, phenol adduct crystals of BPTMC are added to the starting liquid mixture so that phenol adduct crystals of BPTMC are already present in the starting liquid mixture before the start of the reaction. Subsequently an acid catalyst is introduced into the reaction vessel and then a mixture of TMC and phenol to start the reaction while the reaction mixture is maintained at the temperature in the range above mentioned throughout the reaction.

Preferably, the reaction of phenol with TMC is started in the presence of an acid catalyst in a slurry which contains phenol adduct crystals of BPTMC and then the reaction is continued in the slurry. In this way, the BPTMC generated in the reaction forms adduct crystals with phenol immediately in the reaction mixture. Thus, the reaction is carried out in the slurry from the start to the completion of the reaction.

According to the invention, at least a part of the secondary crystallization filtrate, preferably the entire secondary crystallization filtrate which is obtained in the secondary crystallization step and contains phenol and BPTMC as described hereunder, is added to the starting liquid mixture so that phenol adduct crystals of BPTMC are present in advance before the start of the reaction.

The amount of BPTMC present in the starting liquid mixture before the start of the reaction depends on the temperature of the starting liquid mixture, but it is usually not less than 3% by weight, preferably in the range of 5–15% by weight of the phenol in the starting liquid mixture so that BPTMC readily forms phenol adduct crystals therein.

The ratio of phenol (A) and TMC (B) both used as raw materials in the reaction step is in the range of 4 to 9, preferably in the range of 6 to 8, in terms of A/B molar ratio. In addition, aromatic hydrocarbons such as toluene, xylene or mesitylene may be used together with phenol in an amount of 10% by weight or less based on the reaction mixture.

According to the process of the invention, water is used in the reaction step together with phenol usually in an amount of 3–20% by weight, preferably in an amount of 5–15% by weight, based on the amount of phenol used in the reaction step. The water serves to form hydrated phenol and hence to lower the freezing point of phenol, and besides, it serves to improve the absorption of hydrogen chloride gas of the reaction mixture when it is used as a catalyst, thereby to increase the reaction velocity.

The acid catalyst used in the invention is mineral acids such as hydrogen chloride gas, concentrated hydrochloric acid, concentrated sulfuric acid, phosphoric acid or methanesulfonic acid. These may be used singly or as a mixture of two or more. Among these mineral acids, hydrogen chloride gas is particularly preferred.

It is possible to react phenol with TMC by using a mineral acid only as a catalyst, but it is preferred to use a thiol as a promoter together with the mineral acid. The use of a promoter accelerates the reaction. Alkyl mercaptans of 1–12 carbons are preferred as the thiol, and as such thiols, there may be mentioned, for example, methyl mercaptan, ethyl mercaptan, n-octyl mercaptan or n-lauryl mercaptan or alkali metal salts such as sodium salts of these alkyl mercaptans. Among these, sodium methyl mercaptide is in particular preferred. The thiol is used usually in an amount of 1–30 mol %, preferably 2–10 mol %, based on TMC used.

When hydrogen chloride gas is used as an acid catalyst, it is preferred that the reaction is carried out in a reaction vessel in such a manner that the concentration of hydrogen chloride gas in the gas phase in the reaction vessel is in the range of 75–90% by volume so that the yield of the desired reaction product improves, although the reason therefore has not yet been clarified.

In order to maintain the concentration of hydrogen chloride gas in the gas phase in the reaction vessel at 75–90% by volume, the concentration of hydrogen chloride gas is maintained at 75–90% by volume of the total amount (100% by volume) of an inert gas such as nitrogen gas and hydrogen chloride gas in the vapor phase in the reaction vessel under the atmospheric pressure, for example.

In the process of the invention, the reaction temperature is usually in the range of 15–40°, preferably in the range of 20–30° C. When the reaction is carried out at the temperature as mentioned above, the phenol adduct crystals of BPTMC formed in the reaction are neither decomposed nor dissolved in the reaction mixture. Further, the reaction is carried out usually under the atmospheric pressure, however, the reaction may be carried out under increased pressures.

The manner in which phenol is reacted with TMC is not specifically limited, however, as mentioned hereinbefore, it is preferred that phenol is reacted with TMC in the following manner. That is, the secondary crystallization filtrate which is described hereinafter is added to the starting liquid mixture composed of phenol and water (i.e., hydrated phenol) in a reaction vessel to prepare a slurry containing phenol adduct crystals of BPTMC as described hereinbefore. Hydrogen chloride gas is then introduced into the reaction vessel and the concentration of hydrogen chloride gas is adjusted at 75–90% by volume in the gas phase of the reaction vessel. In this way, the hydrogen chloride gas is made into contact with the slurry while a mixture of TMC and phenol is added dropwise into the slurry in the reaction vessel to start the reaction, and the reaction is continued.

(Neutralization Step)

After the reaction, the resulting reaction mixture is neutralized with an alkali in the neutralization step. The alkali used includes hydroxides of alkali metals such as sodium hydroxide or potassium hydroxide. An aqueous solution of sodium hydroxide in a concentration of about 10–20% by weight is preferably used. The alkali is added to the reaction mixture so that it has finally a pH of 5 to 8, preferably 5 to 6.5 and the reaction mixture is weakly acidic.

According to the invention, it is preferred that the resulting reaction mixture is neutralized with an alkali and on one hand it is heated. Accordingly, the reaction mixture may be neutralized and heated simultaneously, that is, the reaction mixture may be heated while an alkali is added to the reaction mixture. Alternatively the resulting reaction mixture may be treated in two steps. That is, an alkali is added to the reaction mixture, and then it is heated.

However, it is preferred that in the first step an alkali is added to the reaction mixture while it is maintained at a temperature of 20–60° C., preferably of 20–50° C., so that the reaction mixture remains to be a slurry and contains phenol adduct crystals therein, followed by stirring for 30 minutes to one hour. Then, in the second step the reaction mixture is heated to at a temperature of 60–100° C., preferably of 80–95° C., while it is stirred, thereby dissolving the phenol adduct crystals to convert the neutralized reaction mixture to a solution.

The alkali, for example, in the form of an aqueous solution of sodium hydroxide, may be added to the reaction mixture in a lump or may be added in portions. However, it is preferred that the alkali is added to the reaction mixture each in an appropriate amount both in the first and second step in order that the pH of the reaction mixture is easily controlled. According to the invention, the reaction mixture is neutralized while it is heated so that it comes to a solution, and as a result, the finally obtained product is substantially free not only from trace impurities but also from reduction of purity and hue.

(Primary Crystallization and Filtration Step)

As described above, the reaction mixture is neutralized while it is heated, and then water is removed from the resulting solution. As the primary crystallization and filtration step, the thus obtained oily substance is cooled to a temperature of 20–40° C., preferably of 25–35° C., to crystallize the desired phenol adduct crystals of BPTMC out of the oily substance. The phenol adduct crystals of BPTMC are filtered and separated from the oily substance by suitable means, for example, by centrifugation while a primary crystallization filtrate is obtained.

This primary crystallization filtrate usually contains unreacted phenol as the greater part of organic components and a small amount of BPTMC dissolved therein. In more detail, the primary crystallization filtrate is usually composed of 80–90% by weight of organic components comprised of unreacted phenol, BPTMC dissolved in the unreacted phenol and others (by-products such as isomers or polymeric materials) and 10–20% by weight of water. The organic components are composed of, by way of example, 80–90% by weight of phenol, 3–7% by weight of BPTMC and 5–10% by weight of the others as mentioned above.

Preferably, a small amount of alkali such as sodium hydroxide is added to the primary crystallization filtrate, and the filtrate is then heated to a temperature of about 150–250° C. under reduced pressure to decompose BPTMC remaining in the filtrate as well as to recover the phenol.

(Secondary Crystallization Filtration Step)

The phenol adduct crystals of BPTMC obtained in the primary crystallization filtration step are further purified by recrystallization in the secondary crystallization filtration step. In more detail, the phenol adduct crystals of BPTMC obtained in the primary crystallization filtration step are first added to a crystallization solvent, heated and dissolved in the solvent.

The solvent preferably used includes aromatic hydrocarbon solvents. Any aromatic hydrocarbon solvent may be used as long as it dissolves BPTMC therein when the solvent is heated and it has reduced solubility of BPTMC therein when the solvent is cooled. Accordingly, relatively low boiling point aromatic hydrocarbon solvents such as benzene, toluene, xylene or ethylbenzene are used, and toluene is preferably used. The most preferred crystallization solvent is a mixture of such an aromatic hydrocarbon solvent as mentioned above and water.

When such a mixture of an aromatic hydrocarbon solvent and water is used as a crystallization solvent, it is heated to a temperature of about 100–130° C. under a pressure of, for example, 0.2–0.4 MPa, to dissolve the phenol adduct crystals of BPTMC therein.

The mixture of an aromatic hydrocarbon solvent and water is usually contains 55–75% by weight, preferably 60–70% by weight of aromatic hydrocarbon solvent.

Such a crystallization solvent is used usually in an amount of 150–400 parts by weight, preferably in an amount of 200–300 parts by weight, in relation to 100 parts by weight of the phenol adduct crystals of BPTMC. When the crystallization solvent is used in an amount of more than 400 parts by weight in relation to 100 parts by weight of the phenol adduct crystals of BPTMC, the volume efficiency in the purification operation decreases while when the crystallization solvent is used in an amount of less than 150 parts by weight in relation to 100 parts by weight of the adduct crystals, it is difficult to remove sufficiently residual phenol and impurities from the resulting BPTMC, and hence it is difficult to obtain the desired product in high purity.

In this way, the residual phenol is easily removed from BPTMC by using the aromatic hydrocarbon solvent as a secondary crystallization solvent in the secondary crystallization and filtration step according to the invention, and in addition, the solubility of BPTMC in the crystallization solvent increases to improve the volume efficiency in the purification process by using water in combination with the aromatic hydrocarbon solvent.

According to the invention, as described above, after the adduct crystals are dissolved in a crystallization solvent comprised of the aromatic hydrocarbon solvent and water and water is removed from the resulting mixture, the resulting oily substance is cooled to crystallize BPTMC, followed by filtering the crystals, thereby providing high purity BPTMC.

(Filtrate Recycling Step)

A secondary crystallization filtrate is obtained in the secondary crystallization and filtration step as described above. It is preferred that the aromatic hydrocarbon solvent and water are removed from the secondary crystallization filtrate to provide secondary filtrate residue. Then, according to the invention, at least a part of the secondary filtrate residue, preferably 50–100% and most preferably the entire secondary filtrate residue is recycled back for reuse to the starting liquid mixture used in the reaction step.

This recycle or reuse of the secondary filtrate residue is useful not only from the standpoint of reuse of raw materials but also useful to form phenol adduct crystals of BPTMC in the starting liquid mixture by returning the secondary filtrate residue to the starting liquid mixture since the secondary filtrate residue contains relatively a large amount of BPTMC. The recycle of the secondary filtrate residue is also useful for recovery of BPTMC. Further according to the invention, at least a part of the primary crystallization filtrate obtained in the primary crystallization and filtration step may be also recycled to the reaction step together with the secondary filtrate residue.

According to the invention, the secondary filtrate residue may be recycled many times to the starting liquid mixture for reuse. On the other hand, when the primary crystallization filtrate is recycled, by-products formed such as isomers and polymeric material are accumulated in the primary crystallization filtrate during recycling. Therefore, when the entire primary crystallization filtrate is recycled, it is preferred that it be recycled three times or less. However, when a part of the primary crystallization filtrate is recycled, it is preferred that about 50–70% is recycled.

Industrial Applicability

As described above, the process of the invention comprises the reaction step wherein phenol is reacted with TMC in a slurry which contains phenol adduct crystals of BPTMC therein in the presence of an acid catalyst, the neutralization step, primary crystallization and filtration step, secondary crystallization and filtration step and secondary filtrate recycling step. Thus, through the combination of the steps as mentioned above, the process provides BPTMC which has a high purity of not less than 99.8%, a phenol content of not more than 200 ppm, trace impurities of sodium, chlorine and sulfur each not more than 1 ppm, and is not colored, in a yield of not less than 75%.

Further according to the invention, since at least a part of the secondary filtrate residue is recycled back to the reaction step for reuse, the formation of phenol adduct crystals of BPTMC are promoted, and in addition, the recovery of BPTMC dissolved in the phenol in the secondary crystallization and filtration step is also facilitated.

EXAMPLES

The invention is described in more detail with reference to examples, but the invention is not limited these examples.

Example 1

87.5 g (0.93 mol) of phenol, 16.9 g of water, 0.5 g of 75% aqueous solution of phosphoric acid and 38.5 g of secondary filtrate residue which had been obtained in the secondary crystallization and filtration step as described hereunder were placed in a one liter capacity four-necked flask provided with a thermometer, a dropping funnel, a reflux condenser and a stirrer to prepare a slurry containing phenol adduct crystals of BPTMC. The secondary filtrate residue was found to be composed of 25.7 g of phenol and 12.8 g of BPTMC by liquid chromatographic analysis.

The slurry was adjusted at a temperature of 20°. After the inside the flask was replaced by nitrogen gas, hydrogen chloride gas was introduced into the flask under stirring. After the gas composition in the reaction vessel was analyzed and the volume concentration of hydrogen chloride gas was adjusted at 80%, 4.2 g of 15% aqueous solution of sodium methyl mercaptide was added dropwise to the slurry while the slurry was maintained at a temperature of 20° C., and then a mixture of 112.8 g (1.2 mol) of phenol and 42.0 g (0.3 mol) of TMC was added dropwise to the slurry over a period of six hours. The reaction mixture was found to increase in temperature during the addition, and when the addition was completed, the temperature was found to be 40° C. Then, the reaction was further continued at a temperature of 40° C. for anther three hours under stirring (reaction step).

After the reaction, the resulting reaction mixture was analyzed by liquid chromatography. The production yield (mol of BPTMC produced/mol of starting TMC used) was found 91.6%.

After the reaction, 18% aqueous solution of sodium hydroxide was added to the reaction mixture so that it was neutralized to have a pH of 6.5 while it was maintained at a temperature of 40–50° C. The thus neutralized reaction mixture was heated to a temperature of 95° C. so that the phenol adduct crystals of BPTMC formed were dissolved therein (neutralization step).

Water was removed from the reaction mixture, and the resulting oily substance was cooled to a temperature of 30° C. to crystallize adduct crystals. 129.4 g of the adduct crystals were collected by filtration while a primary crystallization filtrate was obtained (primary crystallization and filtration step). The hue of the resulting adduct crystals was found to be 40 as measured as 20% solution in methanol according to the APHA (American Public Health Association) standards.

Then, a mixture of 129.4 g of phenol adduct crystals of BPTMC, 194.1 g of toluene and 129.4 g of water was placed in a one liter capacity autoclave provided with a thermometer, a manometer and stirrer. After the inside atmosphere of the autoclave was replaced by nitrogen gas, the autoclave was closed, and then the inside was raised to a temperature of 120° C. with stirring to dissolve the adduct crystals in the mixture. The stirring was then stopped, and the mixture was left standing for 30 minutes. Water was separated from the mixture and the resulting oily substance was cooled to a temperature of 50° C. to crystallize BPTMC crystals out of the mixture. The oily substance was then centrifuged to collect BPTMC crystals while it was kept at a temperature of 50° C. (secondary crystallization and filtration step).

The thus obtained BPTMC crystals were dried at a temperature of 110° C. under a pressure of 20 mmHg for four hours to evaporate the solvent to provide 86 g of white BPTMC crystals. The yield was 78.7 mol % based on the starting TMC.

The BPTMC crystals were found to have a hue of 10 as measured as 10% solution in methanol according to the APHA standards, a purity of 99.9% by liquid chromatographic analysis and a phenol content of 100 ppm. The trace impurities contained were 0.4 ppm of sodium (atomic absorption spectrometry), 0.27 ppm of chlorine (inductively coupled plasma spectrometry) and 0.6 ppm of sulfur (inductively coupled plasma spectrometry).

Example 2

86.0 g (0.9 mol) of phenol, 16.9 g of water, 0.5 g of 75% aqueous solution of phosphoric acid and 34.7 g of secondary filtrate residue which was obtained by removing toluene by distillation from the secondary crystallization filtrate which had been obtained in the same manner as in Example 1 were placed in a one liter capacity four-necked flask provided with a thermometer, a dropping funnel, a reflux condenser and a stirrer to prepare a slurry containing phenol adduct crystals of BPTMC. The secondary crystallization filtrate was found to be composed of 26.8 g (1.2 mol) of phenol and 7.9 g of BPTMC by liquid chromatographic analysis.

The slurry was adjusted at a temperature of 20° C. After the inside the flask was replaced by nitrogen gas, hydrogen chloride gas was introduced into the flask under stirring. The gas composition in the reaction vessel was analyzed and the volume concentration of hydrogen chloride gas was adjusted at 80%.

4.2 g of 15% aqueous solution of sodium methyl mercaptide was added dropwise to the slurry while the slurry was maintained at a temperature of 20° C. A mixture of 129.4 g of the primary filtrate residue which was obtained by removing water from the primary crystallization filtrate which had been obtained in the sama manner as in Example 1 and 42.0 g (0.3 mol) of TMC was added dropwise to the slurry over a period of six hours. The primary filtrate residue was found to be composed of 112.8 g of phenol, 6.8 g of BPTMC and 9.8 g of others by liquid chromatographic analysis. The reaction mixture was found to increase in temperature during the addition, and when the addition was completed, the temperature was found to be 40° C. Then, the reaction was further continued at a temperature of 40° C. for anther three hours under stirring (reaction step).

After the reaction, the resulting reaction mixture was analyzed by liquid chromatography and the production yield of BPTMC was found to be 96.8 mol %. The reaction mixture was worked up in the same manner as in Example 1 to provide 127 g of phenol adduct crystals of BPTMC of which hue was found to be 50 as measured as 20% methanol solution according to the APHA standards.

The reaction mixture containing the thus obtained phenol adduct crystals of BPTMC were purified by the neutralization step, primary crystallization and filtration step and secondary crystallization and filtration step in the same manner as in Example 1 to provide 82 g of white BPTMC crystals. The production yield was 80.5 mol % based on the starting TMC.

The crystals were found to have a hue of 10 as measured as 10% methanol solution according to the APHA standards, a purity of 99.9% and a phenol content of 100 ppm by liquid chromatographic analysis. The trace impurities contained were 0.3 ppm of sodium (atomic absorption spectrometry), 0.5 ppm of chlorine (inductively coupled plasma spectrometry) and 0.6 ppm of sulfur (inductively coupled plasma spectrometry).

Comparative Example 1

112.8 g (1.2 mol) of phenol, 16.9 g of water and 0.5 g of 75% aqueous solution of phosphoric acid were placed in the same one liter capacity four-necked flask as that used in the Example 1, and the reaction was carried out otherwise in the same manner as in Example 1.

As a result, BPTMC was produced in a production yield of 87.9 mol %, and 111 g of phenol adduct crystals of BPTMC were obtained in the same manner. 111 g of phenol adduct crystals of BPTMC and 77 g of water were placed in a one liter capacity autoclave, and after the inside atmosphere was replaced by nitrogen gas, the autoclave was closed, and the inside the autoclave was raised to a temperature of 140° C. The mixture was then cooled to a temperature of 80° C. and subjected to centrifugation. The obtained crystals were dried at a temperature of 120° C. under a pressure of 20 mmHg for four hours to provide 70 g of pale yellow BPTMC crystals.

The crystals were found to have a purity of 99.5% and a phenol content of 500 ppm by liquid chromatographic analysis, and a hue of 30 as measured as 10% methanol solution according to the APHA standards.

What is claimed is:

1. A process for production of high purity 1,1-bis(4-hydroxyphenyl)-3,3,5-trimethylcyclohexane which comprises:

(a) a reaction step wherein phenol is reacted with 3,3,5-trimethylcyclohexanone in a slurry containing phenol adduct crystals of 1,1-bis(4-hydroxyphenyl)-3,3,5-trimethylcyclohexane in the presence of an acid catalyst;

(b) a neutralization step wherein after the reaction, the resulting reaction mixture in the form of slurry is neutralized with an alkali to a pH of 5 to 8 while it is heated so that it is converted to a solution;

(c) a primary crystallization and filtration step wherein the resulting solution is cooled and the resulting phenol adduct crystals of 1,1-bis(4-hydroxyphenyl)-3,3,5-trimethylcyclohexane are collected by filtration;

(d) a secondary crystallization and filtration step wherein the adduct crystals obtained in the primary crystallization and filtration step are heated in a crystallization solvent to dissolve the adduct crystals therein to prepare a solution and then the solution is cooled to crystallize the 1,1-bis(4-hydroxyphenyl)-3,3,5-trimethylcyclohexane out of the solution, followed by collecting the crystals by filtration;

(e) a filtrate recycling step wherein at least a part of the secondary crystallization filtrate obtained in the secondary crystallization and filtration step is returned to the reaction step.

2. The process as claimed in claim 1 wherein phenol and 3,3,5-trimethylcyclohexanone are used in a phenol/3,3,5-trimethylcyclohexanone molar ratio of 4 to 9 in the reaction step.

3. The process as claimed in claim 1 wherein the reaction is carried out at a temperature in the range of 15° C. to 40° C. in the reaction step.

4. The process as claimed in claim 1 wherein the acid catalyst is hydrogen chloride gas.

* * * * *